(12) United States Patent
Craig et al.

(10) Patent No.: US 10,792,064 B2
(45) Date of Patent: Oct. 6, 2020

(54) ENERGY-BASED SURGICAL INSTRUMENT FOR TREATING TISSUE

(71) Applicant: COVIDIEN LP, Mansfield, MA (US)

(72) Inventors: Jason L. Craig, Loveland, CO (US);
Ryan C. Artale, Crested Butte, CO (US); Thomas W. Meiser, Lakewood, CO (US); Roland Jeffrey Wyatt, Bozeman, MT (US)

(73) Assignee: Covidien LP, Mansfield, MA (US)

( * ) Notice: Subject to any disclaimer, the term of this patent is extended or adjusted under 35 U.S.C. 154(b) by 518 days.

(21) Appl. No.: 15/670,101

(22) Filed: Aug. 7, 2017

(65) Prior Publication Data

US 2018/0042637 A1 Feb. 15, 2018

Related U.S. Application Data

(60) Provisional application No. 62/374,115, filed on Aug. 12, 2016.

(51) Int. Cl.
*A61B 17/32* (2006.01)
*A61B 17/29* (2006.01)
(Continued)

(52) U.S. Cl.
CPC ...... *A61B 17/320092* (2013.01); *A61B 17/29* (2013.01); *A61B 17/295* (2013.01);
(Continued)

(58) Field of Classification Search
CPC .............. A61B 17/29; A61B 17/295; A61B 17/320068; A61B 17/2909;
(Continued)

(56) References Cited

U.S. PATENT DOCUMENTS 5,322,055 A   6/1994  Davison et al.
5,637,110 A   6/1997  Pennybacker et al.
(Continued)

FOREIGN PATENT DOCUMENTS

DE    29713490 U1   10/1997
DE    19713067 A1   10/1998
WO    2016-015233 A1   2/2016

OTHER PUBLICATIONS

Extended European Search Report issued in corresponding application No. 17185855.8 dated Dec. 13, 2017.

*Primary Examiner* — Diane D Yabut
*Assistant Examiner* — Majid Jamialahmadi
(74) *Attorney, Agent, or Firm* — Carter, DeLuca & Farrell LLP

(57) ABSTRACT

A surgical instrument includes a housing, an end effector, a movable handle, and a drive assembly. The movable handle includes first and second cantilever spring arms and is movable relative to the housing between a spaced-apart position and an approximated position. The first cantilever spring arm is flexed upon movement of the movable handle from the spaced-apart position towards the approximated position to bias the movable handle towards the spaced-apart position. The drive assembly is operably coupled between the movable handle and the end effector such that movement of the movable handle from the spaced-apart position towards the approximated position moves the end effector from an open position towards a clamping position for clamping tissue. The second cantilever spring arm is flexed upon application of a threshold pressure to tissue clamped by the end effector to control an amount of pressure applied to tissue clamped by the end effector.

19 Claims, 4 Drawing Sheets

(51) Int. Cl.
*A61B 17/295* (2006.01)
*A61B 90/00* (2016.01)
*A61B 17/28* (2006.01)
*A61B 17/00* (2006.01)
*G10K 11/22* (2006.01)

(52) U.S. Cl.
CPC ...... *A61B 17/320068* (2013.01); *A61B 90/03* (2016.02); *G10K 11/22* (2013.01); *A61B 2017/0046* (2013.01); *A61B 2017/00402* (2013.01); *A61B 2017/00477* (2013.01); *A61B 2017/2825* (2013.01); *A61B 2017/2912* (2013.01); *A61B 2017/2917* (2013.01); *A61B 2017/2919* (2013.01); *A61B 2017/320074* (2017.08); *A61B 2017/320094* (2017.08); *A61B 2017/320095* (2017.08)

(58) Field of Classification Search
CPC .... A61B 2017/2917; A61B 2017/2919; A61B 2017/2912; A61B 2017/2925; A61B 2017/2918
See application file for complete search history.

(56) References Cited

U.S. PATENT DOCUMENTS

| | | |
|---|---|---|
| 5,653,721 A | 8/1997 | Knodel et al. |
| 5,776,155 A | 7/1998 | Beaupre et al. |
| 5,897,523 A | 4/1999 | Wright et al. |
| 5,906,628 A | 5/1999 | Miyawaki et al. |
| 5,944,737 A | 8/1999 | Tsonton et al. |
| 5,947,984 A | 9/1999 | Whipple |
| 6,024,750 A | 2/2000 | Mastri et al. |
| 6,214,023 B1 | 4/2001 | Whipple et al. |
| 6,589,200 B1 | 7/2003 | Schwemberger et al. |
| 7,799,045 B2 | 9/2010 | Masuda |
| 7,846,155 B2 | 12/2010 | Houser et al. |
| 8,419,757 B2 | 4/2013 | Smith et al. |
| 8,444,664 B2 | 5/2013 | Balanev et al. |
| 8,708,210 B2 * | 4/2014 | Zemlok ............ A61B 17/2909 227/175.1 |
| 8,773,001 B2 | 7/2014 | Wiener et al. |
| 2012/0116262 A1 | 5/2012 | Houser et al. |
| 2012/0116264 A1 | 5/2012 | Haberstich et al. |
| 2012/0116388 A1 | 5/2012 | Houser et al. |
| 2012/0116394 A1 | 5/2012 | Timm et al. |
| 2012/0116396 A1 | 5/2012 | Price et al. |
| 2012/0116433 A1 | 5/2012 | Houser et al. |
| 2014/0025070 A1 | 1/2014 | Kerr et al. |
| 2014/0284313 A1 | 9/2014 | Allen, IV et al. |
| 2015/0148831 A1 | 5/2015 | Faller et al. |
| 2015/0209060 A1 | 7/2015 | Dmuschewsky |
| 2017/0296199 A1* | 10/2017 | Beger ................ A61B 17/1608 |

* cited by examiner

ENERGY-BASED SURGICAL INSTRUMENT FOR TREATING TISSUE

CROSS REFERENCE TO RELATED APPLICATION

The present application claims the benefit of and priority to U.S. Provisional Application Ser. No. 62/374,115, filed on Aug. 12, 2016 the entire contents of which are incorporated herein by reference.

BACKGROUND

Technical Field

The present disclosure relates to energy-based surgical instruments for treating tissue, for example, ultrasonic surgical instruments configured to treat tissue with ultrasonic energy.

Background of Related Art

Energy-based surgical instruments utilize various different forms of energy, e.g., ultrasonic energy, radio frequency (RF) energy, microwave energy, laser energy, thermal energy, etc., to treat tissue in order to achieve a desired tissue effect. Ultrasonic surgical instruments, for example, utilize ultrasonic energy, i.e., ultrasonic vibrations, to treat tissue. More specifically, ultrasonic surgical instruments utilize mechanical vibration energy transmitted at ultrasonic frequencies to treat tissue, e.g., coagulate, cauterize, fuse, seal, cut, desiccate, and/or fulgurate tissue.

Some ultrasonic surgical instruments include a movable jaw member that enables clamping of tissue between the jaw member and an ultrasonic blade. A movable handle, coupled to the jaw member via a drive assembly, is selectively manipulatable to clamp tissue between the jaw member and the ultrasonic blade. Ultrasonic energy produced by a transducer may then be transmitted along a waveguide to the ultrasonic blade at the distal end of the waveguide to treat the clamped tissue.

SUMMARY

As used herein, the term "distal" refers to the portion that is being described which is further from a user, while the term "proximal" refers to the portion that is being described which is closer to a user. Further, to the extent consistent any or all of the aspects detailed herein may be used in conjunction with any or all of the other aspects detailed herein.

In accordance with aspects of the present disclosure, a surgical instrument is provided generally including a housing, an end effector assembly, a movable handle, and a drive assembly. The movable handle includes first and second cantilever spring arms, and is movable relative to the housing between a spaced-apart position and an approximated position. The first cantilever spring arm is flexed upon movement of the movable handle from the spaced-apart position towards the approximated position to thereby bias the movable handle towards the spaced-apart position. The drive assembly is operably coupled between the movable handle and the end effector assembly such that movement of the movable handle from the spaced-apart position towards the approximated position moves the end effector assembly from an open position towards a clamping position for clamping tissue. The second cantilever spring arm is flexed upon application of a threshold pressure to tissue clamped by the end effector assembly to control pressure applied to tissue clamped by the end effector assembly.

In an aspect of the present disclosure, the movable handle is a single, monolithic component. The movable handle may be formed as such by molding.

In another aspect of the present disclosure, the movable handle includes a flange portion extending into and pivotably coupled to the housing and a grasping portion extending from the housing to facilitate manual manipulation by a user. In such aspects, the second cantilever spring arm may extend from the flange portion of the movable handle and/or the first cantilever spring arm may extend from the grasping portion of the movable handle.

In another aspect of the present disclosure, the end effector assembly includes an ultrasonic blade and a clamp arm movable relative to the ultrasonic blade from an open position to a clamping position for clamping tissue therebetween. In such aspects, movement of the movable handle from the spaced-apart position towards the approximated position moves the clamp arm relative to the ultrasonic blade from the open position towards the clamping position.

In still another aspect of the present disclosure, the surgical instrument further includes a transducer assembly removably supported within at least a portion of the housing and an ultrasonic waveguide extending distally from the transducer assembly and the housing. The ultrasonic waveguide defines the ultrasonic blade at a distal end thereof.

In yet another aspect of the present disclosure, the drive assembly includes a mandrel operably coupled to the movable handle and a drive sleeve extending distally from the mandrel and operably coupled to the end effector assembly. In such aspects, a flange portion of the movable handle and the second cantilever spring arm may be positioned between first and second spaced-apart collars of the mandrel. Further still, in such aspects, prior to reaching the threshold pressure, the second cantilever spring arm urges the mandrel to translate through the housing in response to movement of the movable handle towards the approximated position to thereby move the end effector assembly towards the clamping position. On the other hand, upon reaching the threshold pressure, the second cantilever spring arm is flexed against the mandrel in response to movement of the movable handle towards the approximated position such that the mandrel is maintained in position, thereby controlling the application of pressure by the end effector assembly.

In still yet another aspect of the present disclosure, the housing defines a backstop. In such aspects, the first cantilever spring arm is flexed against the backstop upon movement of the movable handle from the spaced-apart position towards the approximated position to thereby bias the movable handle towards the spaced-apart position.

Another surgical instrument provided in accordance with aspects of the present disclosure generally includes a housing, an end effector assembly, a movable handle, and a drive assembly. The movable handle includes a flange portion extending into and pivotably coupled to the housing, a grasping portion extending from the housing to facilitate manual manipulation by a user, and a force-limiting cantilever spring arm extending from the flange portion. The movable handle is movable relative to the housing between a spaced-apart position and an approximated position. The drive assembly includes a mandrel and a drive sleeve. The mandrel is disposed within the housing and defines first and second spaced-apart collars. The flange portion of the movable handle and the force-limiting cantilever spring arm are disposed between the first and second spaced-apart collars of the mandrel. The drive sleeve is engaged to and extends distally from the mandrel to the end effector assembly, wherein a distal end of the drive sleeve operably couples to the end effector assembly. Movement of the movable handle from the spaced-apart position towards the approximated position urges the force-limiting cantilever spring arm into contact with one of the spaced-apart collars of the mandrel to translate the mandrel through the housing, thereby translating the drive sleeve to move the end effector assembly towards the clamping position to apply a clamping pressure to tissue. When the clamping pressure applied to tissue reaches a threshold clamping pressure, further movement of the movable handle from the spaced-apart position towards the approximated position urges the force-limiting cantilever spring arm into contact with one of the spaced-apart collars of the mandrel to flex the force-limiting cantilever spring arm towards the flange portion of the movable handle, inhibiting further translation of the mandrel and the drive sleeve, thereby inhibiting further movement of the end effector assembly towards the clamping position and controlling the application of clamping pressure to tissue.

In an aspect of the present disclosure, the movable handle further includes a biasing cantilever spring arm extending from the grasping portion of the movable handle. The biasing cantilever spring arm is configured to flex upon movement of the movable handle from the spaced-apart position towards the approximated position to thereby bias the movable handle towards the spaced-apart position. In such aspects, the housing may define a backstop such that the biasing cantilever spring arm is flexed against the backstop upon movement of the movable handle from the spaced-apart position towards the approximated position to thereby bias the movable handle towards the spaced-apart position.

In another aspect of the present disclosure, the movable handle is a single, monolithic component, e.g., via molding.

In another aspect of the present disclosure, the end effector assembly includes an ultrasonic blade and a clamp arm movable relative to the ultrasonic blade from an open position to a clamping position for clamping tissue therebetween. The distal end of the drive sleeve is operably coupled to the clamp arm such that movement of the movable handle from the spaced-apart position towards the approximated position moves the clamp arm relative to the ultrasonic blade from the open position towards the clamping position.

In still another aspect of the present disclosure, a transducer assembly is removably supported within at least a portion of the housing and an ultrasonic waveguide extends distally from the transducer assembly and the housing. The ultrasonic waveguide defines the ultrasonic blade at a distal end thereof.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements and.

DETAILED DESCRIPTION

Figure 1:
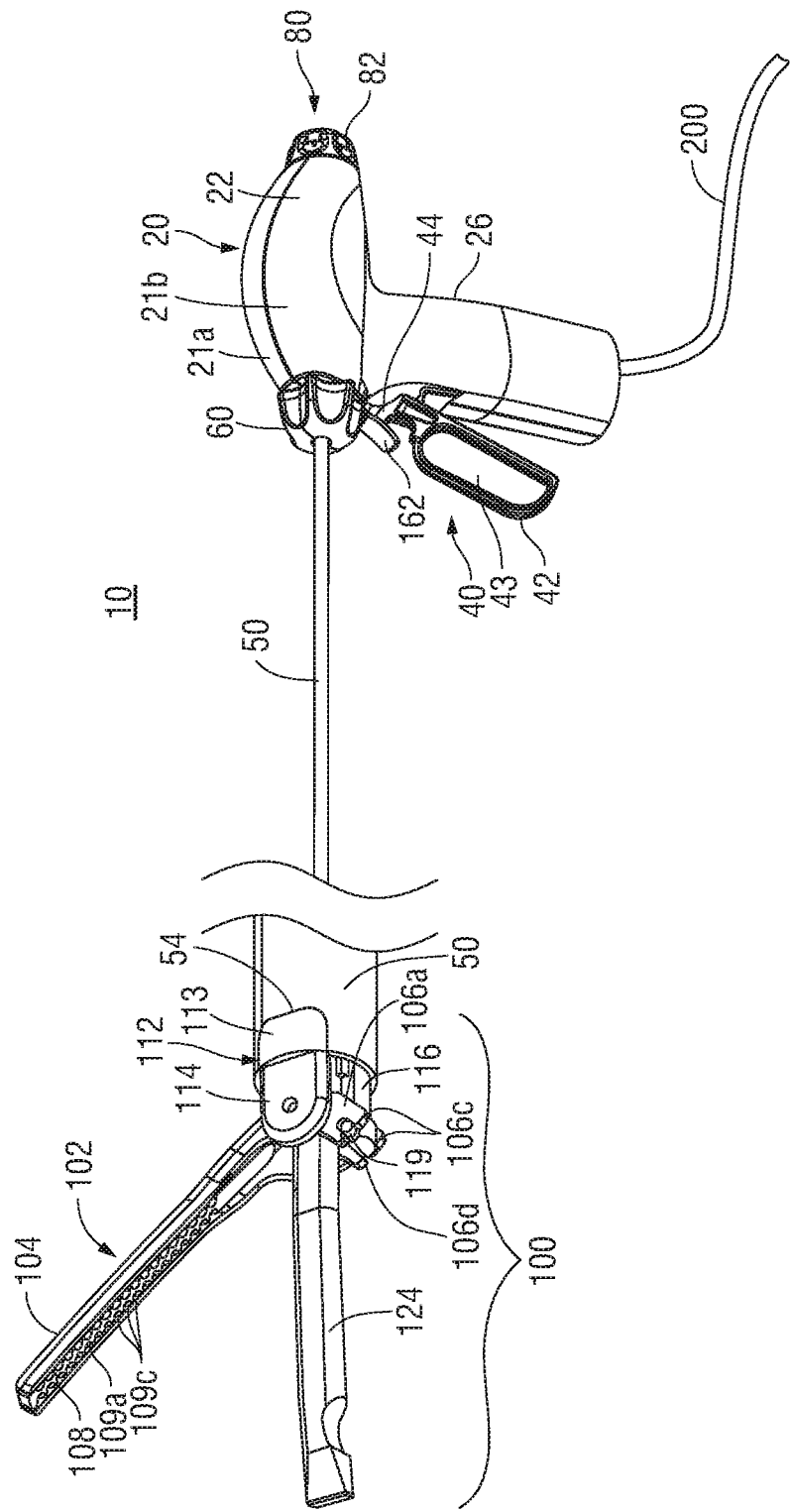
FIG. 1 is a perspective view of an ultrasonic surgical instrument provided in accordance with the present disclosure, wherein the distal end thereof is enlarged to better illustrate the components and features thereof.
Figure 2:
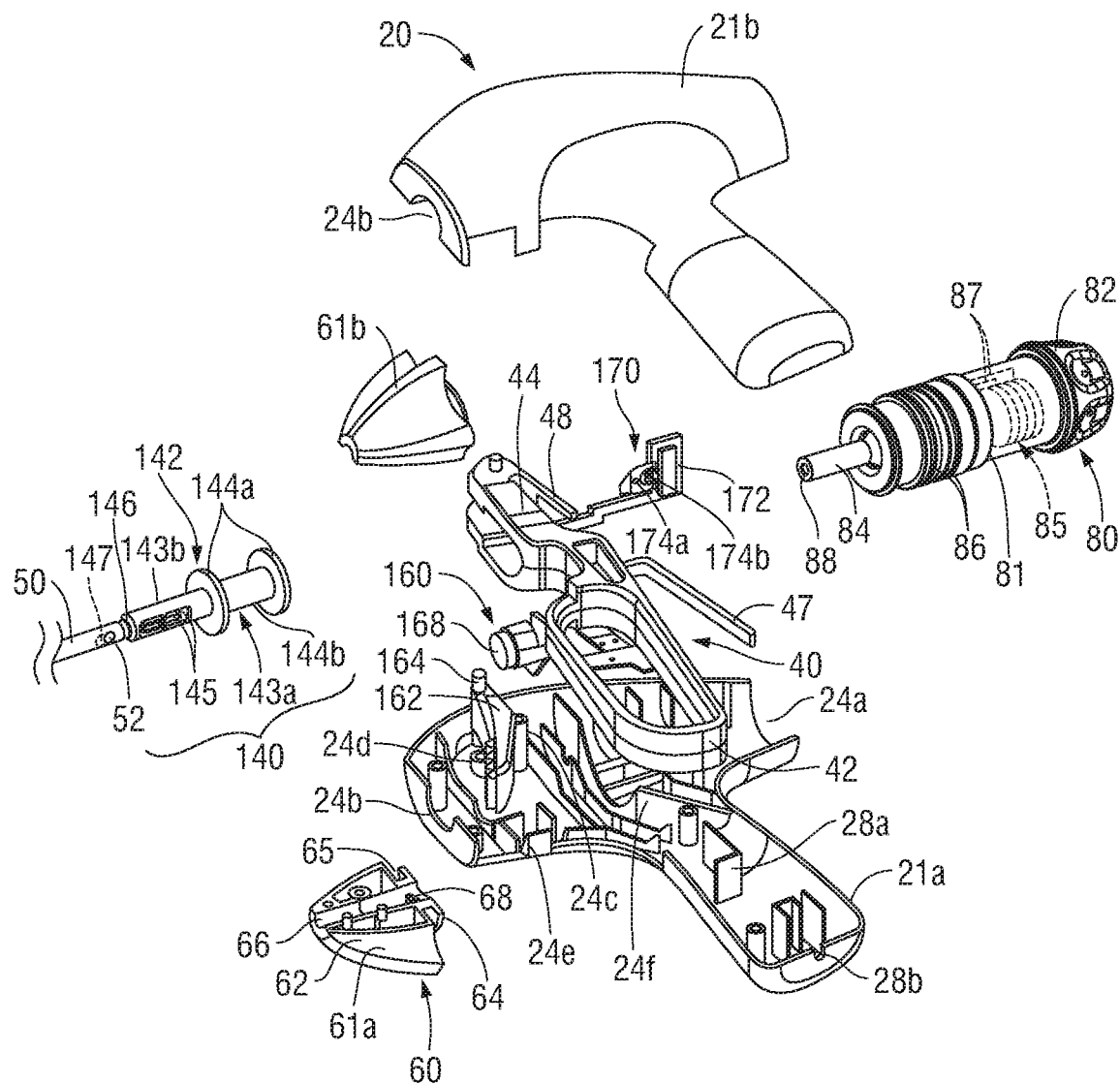
FIG. 2 is an exploded, perspective view of the housing of the ultrasonic surgical instrument of FIG. 1 and the components of the ultrasonic surgical instrument of FIG. 1 operably coupled to and/or within the housing.

Referring generally to FIGS. 1 and 2, an ultrasonic surgical instrument provided in accordance with the aspects and features of the present disclosure is shown generally identified by reference numeral 10. Ultrasonic surgical instrument 10 includes a housing 20, a movable handle 40 operably coupled to housing 20, a shaft 50 extending distally from housing 20, a rotation knob 60 supported on housing 20 and configured for rotating shaft 50 relative to housing 20, a transducer assembly 80 removably supported within housing 20, an end effector assembly 100 disposed at a distal end of shaft 50, a waveguide 120 extending through housing 20 and shaft 50 and operably coupling transducer assembly 80 to end effector assembly 100, a drive assembly 140 extending through housing 20 and shaft 50 and operably coupled between movable handle 40 and end effector assembly 100, and an activation assembly 160 operably coupled to housing 20 for selectively supplying energy to transducer assembly 80 to drive waveguide 120. Ultrasonic surgical instrument 10 further includes a cable 200 configured to connect to a generator (not shown) or other power source for driving transducer assembly 80.

Housing 20 is formed from first and second housing parts 21a, 21b and includes a longitudinally-extending barrel portion 22 and a fixed handle portion 26 extending downwardly from barrel portion 22 in generally perpendicular orientation relative thereto. First and second housing parts 21a, 21b may each be formed via molding or other suitable process, and may be secured to one another via pin-aperture engagement, screws, ultrasonic welding, other suitable mechanisms, or combinations thereof. First and second housing parts 21a, 21b may define mirror-image configurations. Alternatively, some features of housing 20 may be disposed on one housing parts 21a, 21b, other features of housing 20 may be disposed on the other housing part 21a, 21b, and/or some features of housing 20 may be disposed on both housing parts 21a, 21b.

Barrel portion 22 of housing 20 defines a proximal opening 24a configured to removably receive transducer assembly 80; a distal aperture 24b through which shaft 50, drive sleeve 146 of drive assembly 140, and waveguide 120 extend; a first pivot boss 24c defined within each of housing parts 21a, 21b (only the first pivot boss 24c of housing part 21a is shown) and configured to receive one of the pivot protrusions 46 of movable handle 40; a second pivot boss 24d defined within each of housing parts 21a, 21b (only the second pivot boss 24d of housing part 21a is shown) and configured to receive one of the pivot protrusions 164 of trigger 162 of activation assembly 160; a bay 24e configured to support activation button 168 of activation assembly 160; and one or more transducer supports 24f (only the transducer supports 24f of housing part 21a are shown) for rotatably supporting transducer assembly 80 within housing 20.

Fixed handle portion 26 of housing 20 is positioned adjacent movable handle 40 to enable a user to grasp fixed handle portion 26 of housing 20 and manipulate movable handle 40 with a single hand. Fixed handle portion 26 includes a backstop 28a configured to receive the free end of first cantilever spring arm 47 of movable handle 40, and a cable aperture 28b configured to permit passage of cable 200 into housing 20.

Figure 3:
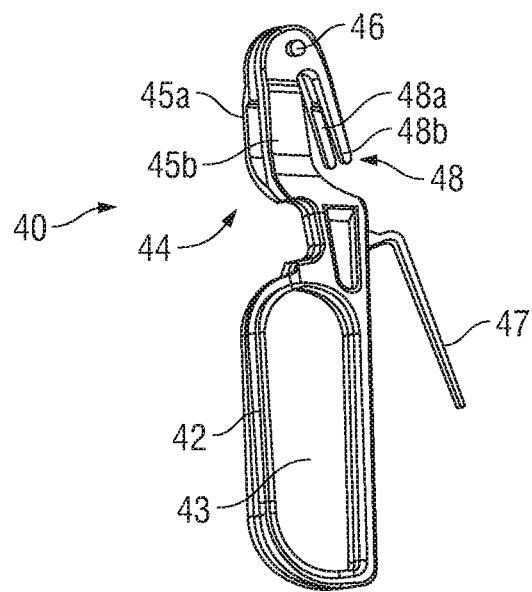
FIG. 3 is a perspective view of the movable handle of the ultrasonic surgical instrument of FIG. 1.

Referring also to FIG. 3, movable handle 40 includes a grasping portion 42, a flange portion 44, and first and second cantilever spring arms 47, 48, respectively. Movable handle 40 is integrally formed as a single component, e.g., via molding or other suitable process. Grasping portion 42 extends downwardly from housing 20 adjacent fixed handle portion 26 of housing 20 and defines a finger loop 43 configured to facilitate grasping and manipulation of movable handle 40, although other configurations of movable handle 40 are also contemplated. First cantilever spring arm 47 extends proximally from grasping portion 42 of movable handle 40 at least partially into fixed handle portion 26 of housing 20, wherein the free end of first cantilever spring arm 47 is seated within backstop 28a of fixed handle portion 26 of housing 20. As a result of this configuration, first cantilever spring arm 47 biases movable handle 40 distally towards a spaced-apart position relative to fixed handle portion 26 of housing 20. As can be appreciated, by integrally forming first cantilever spring arm 47 with movable handle 40, the need for a separate biasing component, e.g., a spring, and associated attachment components for biasing movable handle 40 relative to housing 20 towards the spaced-apart position is obviated.

Flange portion 44 of movable handle 40 extends from grasping portion 42 upwardly into housing 20. Flange portion 44 defines a bifurcated configuration including first and second spaced-apart flange components 45a, 45b, respectively. The bifurcated configuration of flange portion 44 enables position of flange components 45a, 45b on either side of mandrel 142 of drive assembly 140, in operable engagement therewith, as detailed below. Each flange component 45a, 45b of flange portion 44 of movable handle 40 includes a pivot protrusion 46 (only pivot protrusion 46 of flange component 45b is shown) extending outwardly therefrom in a transverse direction and configured for pivotable engagement within one of the first pivot bosses 24c defined within housing parts 21a, 21b of housing 20. Thus, movable handle 40 is pivotable relative to housing 20 from the spaced-apart position to an approximated position, wherein grasping portion 42 of movable handle 40 is disposed in close approximation to fixed handle portion 26 of housing 20. Movable handle 40 further includes second cantilever spring arm components 48a, 48b (collectively second cantilever spring arm 48) extending from each flange component 45a, 45b of flange portion 44 of movable handle 40 in a generally downward and proximal direction. Flange portion 44 of movable handle 40 and second cantilever spring arm 48 of movable handle 40 are configured to operably couple to mandrel 142 of drive assembly 140, as detailed below, such that pivoting of movable handle 40 from the spaced-apart position towards the approximated position pivots clamp arm 102 relative to blade 124 between an open position and a clamping position for clamping tissue therebetween, and such that a clamping pressure applied to tissue clamped between clamp arm 102 and blade 124 is limited so as not to exceed a threshold pressure. As can be appreciated, by integrally forming second cantilever spring arm 48 with movable handle 40, the need for a separate force-limiting mechanism for controlling a clamping pressure applied to tissue is obviated.

Referring again to FIGS. 1 and 2, shaft 50 extends distally through distal aperture 24b of barrel portion 22 of housing 20 and includes end effector assembly 100 disposed at a distal end thereof. Shaft 50 defines is longitudinally fixed relative to housing 20, but is rotatable relative thereto, as detailed below. Shaft 50 is disposed about drive sleeve 146 of drive assembly 140, although it is also contemplated that this configuration be reversed, e.g., wherein drive sleeve 146 is disposed about shaft 50. Shaft 50 defines a tubular configuration without any formed features thereon, which facilities manufacturing, thereby reducing manufacturing costs. Rather than formed features, shaft 50 defines a pair of opposed apertures 52 (only one of which is shown) towards the proximal end thereof, and a pair of cut-out slots 54 (only one of which is shown) open to the distal end of shaft 50, the importance of which is detailed below.

Rotation knob 60 is formed from first and second knob components 61a, 61b each formed via molding or other suitable process and secured to one another via pin-aperture engagement, screws, ultrasonic welding, other suitable mechanisms, or combinations thereof. Rotation knob 60 defines a distal nose 62 configured to abut the proximal end of housing 20, a proximal collar 64 configured for positioning within housing 20, and a neck 65 extending between distal nose 62 and proximal collar 64 and configured to extend through distal aperture 24b of housing 20. Distal nose 62 and proximal collar 64 are dimensioned to inhibit passage thereof through distal aperture 24b of housing 20 such that rotation knob 60, thereby rotatably coupling rotation knob 60 to housing 20.

Rotation knob 60 further includes an internal, longitudinally-extend lumen 66 defined therethrough and a protrusion 68 extending inwardly from each knob component 61a, 61b into lumen 66 (only protrusion 68 of knob component 61a is shown). Shaft 50, drive sleeve 146 of drive assembly, and waveguide 120 are configured to extend at least partially through lumen 66. Protrusions 68 are configured for receipt within opposed apertures 52 of shaft 50 to longitudinally and rotatably fix shaft 50 relative to rotation knob 60. As such, shaft 50 is longitudinally fixed relative to housing 20 but permitted to rotate relative thereto upon rotation of rotation knob 60. Protrusions 68 further extend through opposed slots 147 defined within drive sleeve 146 of drive assembly 140 (only one slot 147 of drive sleeve 146 is shown) to rotatably couple drive sleeve 146 with rotation knob 60 while permitting longitudinal translation of drive sleeve 146 relative to rotation knob 60 (via translation of protrusions 68 through slots 147).

With reference again to FIGS. 1 and 2, transducer assembly 80 is configured for insertion into proximal opening 24a of housing 20 for releasable engagement therein. Transducer assembly 80 includes a generally cylindrical housing 81 including a rotation wheel 82 disposed at the proximal end thereof and a distal horn 84 extending from a distal end thereof. Housing 81 includes a piezoelectric stack 85 disposed therein and a pair of ring contacts 86 disposed thereabout. Ring contacts 86 are electrically coupled to piezoelectric stack 85 via lead wires 87. Distal horn 84 is secured to and extends distally from piezoelectric stack 85 such that ultrasonic vibrations produced by piezoelectric stack 85 are transmitted to distal horn 84. Distal horn 84 defines a threaded female receiver 88 at the distal end thereof for engaging waveguide 120, as detailed below. Upon insertion of transducer assembly 80 into proximal opening 24a of housing 20, housing 81 of transducer assembly 80 is rotatably supported on transducer support(s) 24f, while rotation wheel 82 abuts the proximal end of housing 20 and remains externally thereof such that a user can manipulate rotation wheel 82 to rotate transducer assembly 80 relative to housing 20.

Figure 4:
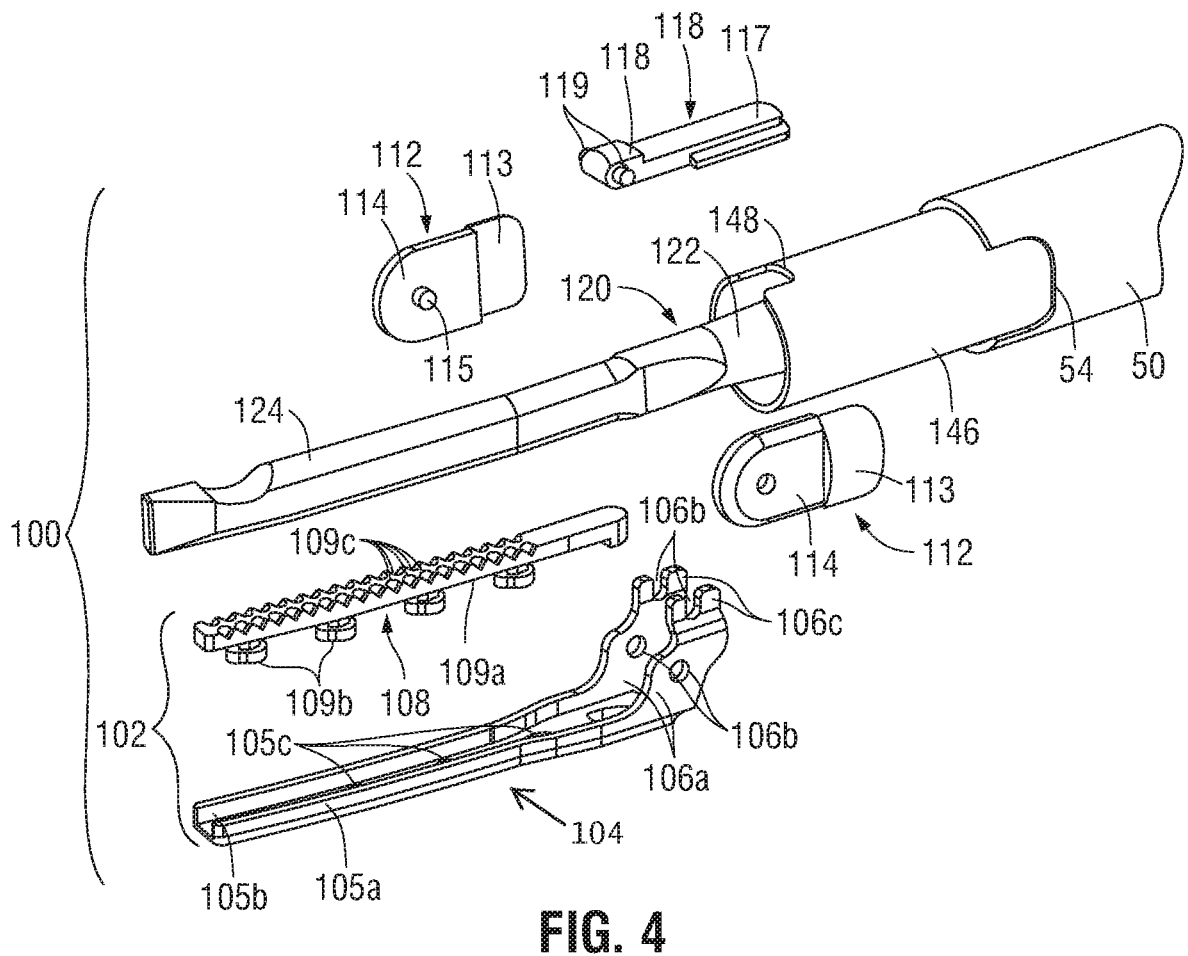
FIG. 4 is an exploded, perspective view of the distal end of the ultrasonic surgical instrument of FIG. 1.

Turning to FIGS. 1 and 4, end effector assembly 100 includes clamp arm 102, blade 124 of waveguide 120 (detailed below), a pair of clevis members 112, and a drive link 116. Clamp arm 102 includes a frame 104 and a tissue pad 108 configured to engage frame 104. Frame 104 may be formed from stamping, metal injection molding (MIM), machining, or other suitable process and defines an elongated distal body 105a and a pair of spaced-apart proximal flanges 106a. Elongated distal body 105a defines a longitudinally-extending track 105b and plurality of apertures 105c.

Tissue pad 108, as mentioned above, is configured for receipt within frame 104. Tissue pad 108, more specifically, includes a body 109a configured for receipt within longitudinally-extending track 105b of elongated distal body 105a of frame 104 and a plurality of fingers 109b configured for receipt within the plurality of apertures 105c of elongated distal body 105a of frame 104 to secure tissue pad 108 relative to frame 104. Tissue pad 108 may be formed from a suitable tissue-contacting material, e.g., PTFE, and may define a plurality of teeth 109c on the tissue-contacting surface 109c thereof.

Each proximal flange 106a of frame 104 of clamp arm 102 defines a pivot aperture 106b and a fork 106c defining a slot 106d between the forked portions thereof. Clevis members 112 may be formed from stamping, metal injection molding (MIM), machining, or other suitable process, and include proximal panels 113 at least partially received within cut-out slots 54 of shaft 50 and secured to shaft 50, e.g., via welding, and distal extensions 114 extending distally from shaft 50. Each distal extension 114 includes an inwardly-extending pivot post 115 configured for receipt within the pivot aperture 106b of one of the proximal flanges 106a of frame 104 of clamp arm 102 to pivotably couple clamp arm 102 to the distal end of shaft 50.

Drive link 116 may be formed from stamping, metal injection molding (MIM), machining, or other suitable process, and includes a proximal base 117 at least partially received within a cut-out slot 148 defined within drive sleeve 146 at the distal end thereof and secured to drive sleeve 146, e.g., via welding. Drive link 116 further includes a distal extension 118 extending distally from drive sleeve 146 and including a pair of outwardly-extending pivot posts 119. Each pivot post 119 is configured for receipt within the slot 106d of the fork 106c of one of the proximal flanges 106a of clamp arm 102 to operably couple drive sleeve 146 to clamp arm 102 at a position offset from the pivotable coupling of clamp arm 102 to shaft 50 such that translation of drive sleeve 146 through and relative to shaft 50 pivots clamp arm 102 relative to shaft 50 and blade 124 between the open and clamping positions.

Referring to FIGS. 1, 2, 4, and 5, waveguide 120 defines a body 122, a blade 124 extending from the distal end of body 122, a proximal connector 126 extending from the proximal end of body 122, and a torque adapter 128 defined about body 122 towards the proximal end thereof. Blade 124 extends distally from drive sleeve 146 of drive assembly 140 and shaft 50 and, as noted above, forms part of end effector assembly 100 in that blade 124 is positioned to oppose clamp arm 102 such that pivoting of clamp arm 102 from the open position to the clamping position enables clamping of tissue between clamp arm 102 and blade 124. Blade 124 may define a linear configuration as shown, or may define a curved configuration wherein the directions of movement of clamp arm 102 between the open and clamping positions are perpendicular to the direction of curvature of blade 124, e.g., wherein blade 124 curves laterally relative to clamp arm 102, and/or where the directions of movement of clamp arm 102 between the open and clamping positions are coaxial or parallel to the direction of curvature of blade 124, e.g., wherein blade 124 curves towards or away from clamp arm 102.

Figure 5:
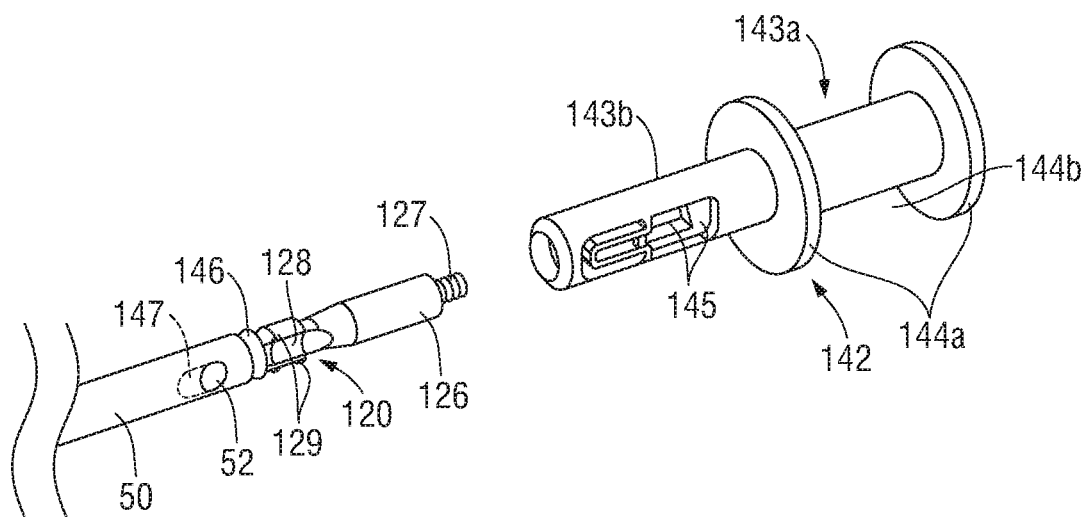
FIG. 5 is a perspective view of the proximal end of the shaft, drive assembly, and waveguide of the ultrasonic surgical instrument of FIG. 1, with the mandrel of the drive assembly separated from the other components.
Figure 6:
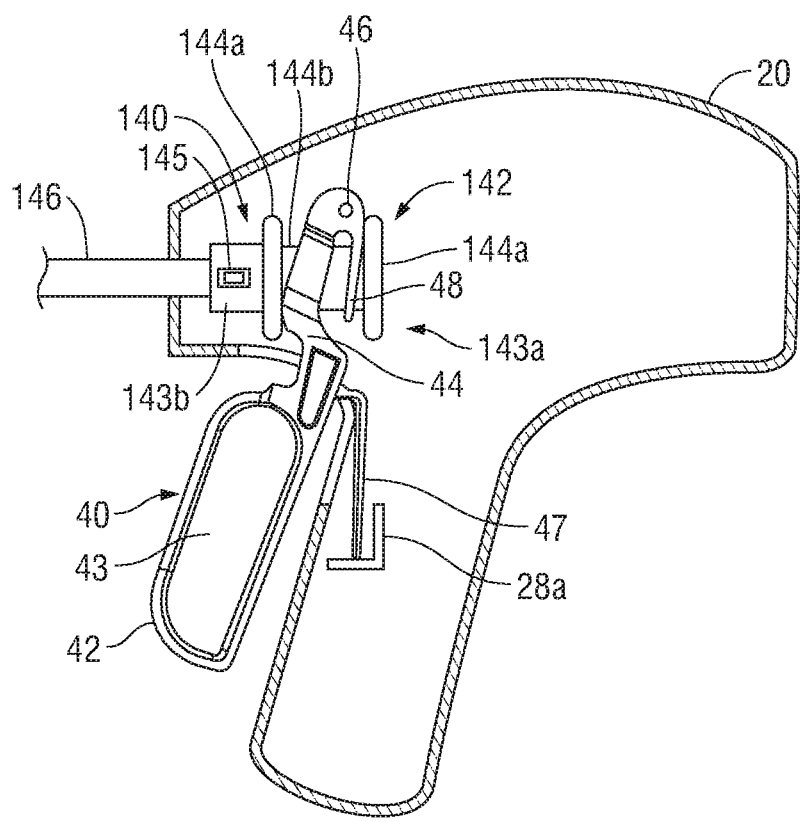
FIG. 6 is a longitudinal, cross-sectional view of the proximal end of the ultrasonic surgical instrument of FIG. 1, with parts removed to unobstructively illustrate the operable coupling of the movable handle with the housing and the drive assembly.

With particular reference to FIGS. 2 and 5, proximal connector 126 of waveguide 120 is configured to enable engagement of waveguide 120 with horn 84 of transducer assembly 80 such that mechanical motion produced by piezoelectric stack 85 is capable of being transmitted along waveguide 120 to blade 124 for treating tissue clamped between blade 124 and clamp arm 102 or positioned adjacent blade 124. To this end, proximal connector 126 includes a threaded male shaft 127 that is configured for threaded engagement within threaded female receiver 88 of horn 84 of transducer assembly 80. Torque adapter 128 of waveguide 120, as shown in FIG. 5, includes a wing 129 extending outwardly from each of the opposing sides thereof. Waveguide 120 is configured to extend through mandrel 142 of drive assembly 140 with wings 129 seated within openings 145 of distal tube 143b of mandrel 142 to rotatably couple waveguide 120 and mandrel 142 with one another.

Referring to FIGS. 2-6, drive assembly 140 includes mandrel 142 and drive sleeve 146. Mandrel 142 includes a body 143a having a pair of spaced-apart collars 144a defining an annular space 144b therebetween. Flange portion 44 of movable handle 40 and second cantilever spring arm 48 of movable handle 40 are configured for receipt within annular space 144b on either side of mandrel 142 between spaced-apart collars 144a thereof to operably couple movable handle 40 to mandrel 142. Mandrel 142 further includes distal tube 143b extending distally from body 143a and fixedly engaged with body 143a. Distal tube 143b defines a pair of opposed openings 145 configured to receive wings 129 of torque adapter 128 of waveguide to rotatably couple waveguide 120 and mandrel 142 with one another.

Drive sleeve 146 of drive assembly 140 is fixedly engaged to mandrel 142, e.g., via welding, molding as a monolithic component, snap-fit engagement, or other suitable process or mechanism, and extends distally from mandrel 142 through shaft 50 to end effector assembly 100. Drive sleeve 146, as noted above, defines opposed slots 147 towards the proximal end thereof for receiving protrusions 68 of rotation knob 60 to rotatably couple drive sleeve 146 with rotation knob 60, and cut-out slot 148 at the distal end thereof that receives and engages drive link 116. Thus, translation of mandrel 142 through housing 20 translates drive sleeve 146 through shaft 50 to pivot clamp arm 102 relative to blade 124 between the open and clamping positions. Drive sleeve 146, like shaft 50, defines a tubular configuration without any formed features thereon, which facilities manufacturing, thereby reducing manufacturing costs. Rather than formed features, drive sleeve 146 defines slots 147 and cut-out slot 148, as detailed above.

Referring to FIGS. 1 and 2, activation assembly 160 includes trigger 162 pivotably coupled to housing 20 and extending therefrom to enable manual manipulation by a user, activation button 168 supported within bay 24e of housing 20 adjacent trigger 162, and a contact assembly 170. Trigger 162 includes a pair of pivot protrusions 164 received within second pivot bosses 24d of housing 20 to pivotably couple trigger 162 relative to housing 20 such that trigger 162 is pivotable relative to housing 20 between an un-actuated, distal position and an actuated, proximal position. Activation button 168 is positioned relative to trigger 162 such that, upon movement of trigger 162 to the actuated position, activation button 168 is depressed to an actuated position. In some embodiments, activation button 168 is configured as a two-mode button wherein pivoting of trigger 162 to a first actuated position actuates activation button 168 to a first actuated position for supplying energy to transducer assembly 80 corresponding to a "LOW" power mode, and wherein pivoting of trigger 162 to a second actuated position actuates activation button 168 to a second actuated position for supplying energy to transducer assembly 80 corresponding to a "HIGH" power mode.

The wires (not explicitly shown) extending through cable 200 are coupled to activation button 168 which, in turn, is coupled to contact assembly 170. More specifically, contact assembly 170 includes a printed circuit board (PCB) 172 operably coupled to activation button 168, and first and second spring contacts 174a, 174b, formed via stamping (or other suitable process) and extending from PCB 172. Each spring contact 174a, 174b includes a bump, e.g., formed thereon via the stamping process, configured to maintain contact, via the spring force of spring contacts 174a, 174b, with one of the ring contacts 86 of transducer assembly 80. This configuration enables the supply of energy, e.g., upon actuation of activation button 168, to transducer assembly 80 regardless of the rotational orientation of transducer assembly 80 relative to housing 20 and enables infinite rotation of transducer assembly 80 in either direction.

Referring generally to FIGS. 1-5, in order to assemble ultrasonic surgical instrument 10, transducer assembly 80, lead by distal horn 84, is inserted through proximal opening 24a of housing 20 until rotation wheel 82 of transducer assembly 80 abuts or is positioned adjacent the proximal end of barrel portion 22 of housing 20. Once this position has been achieved, rotation wheel 82 of transducer assembly 80 is rotated relative to rotation knob 60 (via maintaining one fixed and rotating the other or rotation both in opposite directions) to threadingly engage proximal connector 126 of waveguide 120 within distal horn 84 of transducer assembly 80. A separate torque wrench (not shown) or one integrated into rotation knob 60 may be provided to ensure a proper torque is achieved upon engagement of transducer assembly 80 and waveguide 120.

In use, with general reference to FIGS. 1-6, with clamp arm 102 disposed in the open position, instrument 10 is manipulated and/or end effector assembly 100 rotated, e.g., via rotation knob 60, such that tissue to be treated is disposed between clamp arm 102 and blade 124. Once this position has been achieved, clamp arm 102 may be moved to the clamping position by pivoting movable handle 40 relative to housing 20 from the spaced-apart position towards the approximated position. As moveable handle 40 is initially pivoted towards the approximated position, first cantilever spring arm 48 is flexed towards grasping portion 42 of movable handle 40, while second cantilever spring arm 48, maintained in its initial position, is urged into the more-proximal of the spaced-apart collars 144a of mandrel 142 to thereby translate mandrel 142 and, thus, drive sleeve 146, proximally relative to housing 20 and through shaft 50. Proximal translation of drive sleeve 146 pulls drive link 116 proximally such that clamp arm 102 is pivoted relative to blade 124 from the open position towards the clamping position.

Upon further movement of clamp arm 102 towards the clamping position, increasing clamping pressure is applied to tissue grasped between clamp arm 102 and blade 124, until a threshold pressure is reached. Once this threshold pressure is reached, further movement of movable handle 40 towards the approximated position does not result in further proximal translation of drive sleeve 146 but, rather, results in flexion of second cantilever spring arm 48 towards flange portion 44 of movable handle 40. This flexion of second cantilever spring arm 48 allows movable handle 40 to pivot further towards the approximated position without imparting additional force to drive sleeve 146, thus inhibiting further movement of clamp arm 102 towards the clamping position, thereby controlling the clamping pressure applied to tissue grasped between clamp arm 102 and blade 124 to or below the threshold pressure.

With clamp arm 102 clamping tissue between clamp arm 102 and blade 124 at the threshold pressure, trigger 162 may be actuated from the un-actuated position to the actuated position to actuate activation button 168 (in either the "LOW" or "HIGH" power mode). Actuation of activation button 168 provides energy from cable 200, in the form of a high voltage AC signal, to piezoelectric stack 85 of transducer assembly 80, which converts the high voltage AC signal into mechanical motion that is output from horn 84, along body 122 of waveguide 120, to blade 124. As such, blade 124 is energized to treat tissue grasped between clamp arm 102 and blade 124.

Once tissue has been sufficiently treated, trigger 162 and movable handle 40 are released, whereby movable handle 40 is urged to return towards the spaced-apart position under the bias of first cantilever spring arm 47 to return trigger 162 towards the un-actuated position (under urging from grasping portion 42 of movable handle 40) and clamp arm 102 towards the open position.

While several embodiments of the disclosure have been shown in the drawings, it is not intended that the disclosure be limited thereto, as it is intended that the disclosure be as broad in scope as the art will allow and that the specification be read likewise. For example, although detailed above with respect to ultrasonic surgical instrument 10, it is contemplated that a movable handle 40 having features, e.g., first and second cantilever spring arms 47, 48, for both biasing movable handle 40 towards a spaced-apart position and controlling the pressure applied to tissue, may also be incorporated into other surgical instruments such as, for example, electrosurgical instruments. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a housing;
   an end effector assembly;
   a movable handle including first and second cantilever spring arms, the movable handle movable relative to the housing between a spaced-apart position and an approximated position, wherein, the first cantilever spring arm is flexed upon movement of the movable handle from the spaced-apart position towards the approximated position to thereby bias the movable handle towards the spaced-apart position; and
   a drive assembly operably coupled between the movable handle and the end effector assembly such that movement of the movable handle from the spaced-apart position towards the approximated position moves the end effector assembly from an open position towards a clamping position for clamping tissue, wherein the second cantilever spring arm is flexed upon application of a threshold pressure to tissue clamped by the end effector assembly to control a pressure applied to tissue clamped by the end effector assembly.

2. The surgical instrument according to claim 1, wherein the movable handle is a single, monolithic component.

3. The surgical instrument according to claim 2, wherein the movable handle is molded.

4. The surgical instrument according to claim 1, wherein the movable handle includes a flange portion extending into and pivotably coupled to the housing and a grasping portion extending from the housing to facilitate manual manipulation by a user.

5. The surgical instrument according to claim 4, wherein the second cantilever spring arm extends from the flange portion of the movable handle, and wherein the first cantilever spring arm extends from the grasping portion of the movable handle.

6. The surgical instrument according to claim 1, wherein the end effector assembly includes:
an ultrasonic blade; and
a clamp arm movable relative to the ultrasonic blade from the open position to the clamping position for clamping tissue therebetween, wherein movement of the movable handle from the spaced-apart position towards the approximated position moves the clamp arm relative to the ultrasonic blade from the open position towards the clamping position.

7. The surgical instrument according to claim 6, further comprising:
a transducer assembly removably supported within at least a portion of the housing; and
an ultrasonic waveguide extending distally from the transducer assembly and the housing, the ultrasonic waveguide defining the ultrasonic blade at a distal end thereof.

8. The surgical instrument according to claim 1, wherein the drive assembly includes a mandrel operably coupled to the movable handle and a drive sleeve extending distally from the mandrel and operably coupled to the end effector assembly.

9. The surgical instrument according to claim 8, wherein a flange portion of the movable handle and the second cantilever spring arm are positioned between first and second spaced-apart collars of the mandrel.

10. The surgical instrument according to claim 9, wherein, prior to reaching the threshold pressure, the second cantilever spring arm urges the mandrel to translate through the housing in response to movement of the movable handle towards the approximated position to thereby move the end effector assembly towards the clamping position.

11. The surgical instrument according to claim 10, wherein, upon reaching the threshold pressure, the second cantilever spring arm is flexed against the mandrel in response to movement of the movable handle towards the approximated position such that the mandrel is maintained in position, controlling the application of pressure by the end effector assembly.

12. The surgical instrument according to claim 1, wherein the housing defines a backstop, and wherein, the first cantilever spring arm is flexed against the backstop upon movement of the movable handle from the spaced-apart position towards the approximated position to thereby bias the movable handle towards the spaced-apart position.

13. A surgical instrument, comprising:
a housing;
an end effector assembly;
a movable handle including a flange portion extending into and pivotably coupled to the housing, a grasping portion extending from the housing to facilitate manual manipulation by a user, and a force-limiting cantilever spring arm extending from the flange portion, the movable handle movable relative to the housing between a spaced-apart position and an approximated position; and
a drive assembly, including:
a mandrel disposed within the housing and defining first and second spaced-apart collars, wherein the flange portion of the movable handle and the force-limiting cantilever spring arm are disposed between the first and second spaced-apart collars; and
a drive sleeve engaged to and extending distally from the mandrel to the end effector assembly, a distal end of the drive sleeve operably coupled to the end effector assembly,
wherein, movement of the movable handle from the spaced-apart position towards the approximated position urges the force-limiting cantilever spring arm into contact with one of the spaced-apart collars of the mandrel to translate the mandrel through the housing, thereby translating the drive sleeve to move the end effector assembly towards a clamping position to apply a clamping pressure to tissue, and
wherein, when the clamping pressure applied to tissue reaches a threshold clamping pressure, further movement of the movable handle from the spaced-apart position towards the approximated position urges the force-limiting cantilever spring arm into contact with one of the spaced-apart collars of the mandrel to flex the force-limiting cantilever spring arm towards the flange portion of the movable handle, inhibiting further translation of the mandrel and the drive sleeve, thereby inhibiting further movement of the end effector assembly towards the clamping position and inhibiting application of additional clamping pressure to tissue.

14. The surgical instrument according to claim 13, wherein the movable handle further includes a biasing cantilever spring arm extending from the grasping portion of the movable handle, the biasing cantilever spring arm configured to flex upon movement of the movable handle from the spaced-apart position towards the approximated position to thereby bias the movable handle towards the spaced-apart position.

15. The surgical instrument according to claim 14, wherein the housing defines a backstop, and wherein, the biasing cantilever spring arm is flexed against the backstop upon movement of the movable handle from the spaced-apart position towards the approximated position to thereby bias the movable handle towards the spaced-apart position.

16. The surgical instrument according to claim 14, where the movable handle is a single, monolithic component.

17. The surgical instrument according to claim 16, wherein the movable handle is molded.

18. The surgical instrument according to claim 13, wherein the end effector assembly includes:
an ultrasonic blade; and
a clamp arm movable relative to the ultrasonic blade from an open position to the clamping position for clamping tissue therebetween, wherein the distal end of the drive sleeve is operably coupled to the clamp arm such that movement of the movable handle from the spaced-apart position towards the approximated position moves the clamp arm relative to the ultrasonic blade from the open position towards the clamping position.

19. The surgical instrument according to claim 18, further comprising:
- a transducer assembly removably supported within at least a portion of the housing; and
- an ultrasonic waveguide extending distally from the transducer assembly and the housing, the ultrasonic waveguide defining the ultrasonic blade at a distal end thereof.

* * * * *